United States Patent [19]
Dornburg

[11] Patent Number: 5,869,331
[45] Date of Patent: Feb. 9, 1999

[54] CELL TYPE SPECIFIC GENE TRANSFER USING RETROVIRAL VECTORS CONTAINING ANTIBODY-ENVELOPE FUSION PROTEINS AND WILD-TYPE ENVELOPE FUSION PROTEINS

[75] Inventor: Ralph C. Dornburg, South River, N.J.

[73] Assignee: University of Medicine & Dentistry of New Jersey, Newark, N.J.

[21] Appl. No.: 933,616

[22] Filed: Aug. 28, 1997

Related U.S. Application Data

[63] Continuation of Ser. No. 205,980, Mar. 4, 1994, abandoned, Continuation-in-part of Ser. No. 979,619, Nov. 20, 1992, abandoned.

[51] Int. Cl.⁶ ............................ G12N 15/86; C07K 16/46
[52] U.S. Cl. ...................... 435/320.1; 530/387.3
[58] Field of Search ................ 435/69.1, 320.1, 435/235.1; 530/387.3

[56] References Cited

FOREIGN PATENT DOCUMENTS

| | | |
|---|---|---|
| WO 90 12087 A | 10/1990 | WIPO . |
| WO 92 06180 A | 4/1992 | WIPO . |
| WO 93 00103 | 1/1993 | WIPO . |
| WO 94 06920 | 3/1994 | WIPO . |
| WO 94 12626 A | 6/1994 | WIPO . |

OTHER PUBLICATIONS

Kewalramani, V. N., et al. "Spleen Necrosis Virus, an avian innunossupressive retrovirus, shares a receptor with the type D simian retroviruses", *Journal of Virology*, vol. 66, No. 5, May 1992, pp. 3026–3031.

Riley, S.C. et al. "Preferential expression of variable region heavy chain gene segments by predominant 2,4–dinitrophenyl–specific BALB/c neonatal antibody clonotypes," *Proceedings of the National Academy of Sciences of USA*, vol. 83, No. 8, Apr. 1986, pp. 2589–2593.

Russell, S.J. et al. "Retroviral vectors displaying functional antibody fragments," *Nucleic Acids Res.* (1993), 21(5), pp. 1081–1085.

Te–Hua, T.C., et al. "Cell targeting with retroviral vector particles containing antibody–envelope fusion proteins," *Gene Therapy*, vol. 1, No. 5, Sep. 1994, pp. 292–299.

Marshall, "Gene Therapy's Growing Pains", Science, vol. 269, 25 Aug. 1995, pp. 1050–1055.

Russell et al., "Retrovial Vectors Displaying Fuctional Antibody Fragments", Nuclear Acids Res., vol. 21, No. 5, pp. 1081–1085, 1993.

A. Duatz Miller, "Human Gene Therapy Comes of Age", Nature, vol. 357, Jun. 1992, pp. 455–460.

A. Duatz Miller, "Retrovirus Packagaing Cells", Human Gene Therapy, vol. 1, pp. 5–14, 1990.

Weiss, In "RNA Tumor Viruses", Chapter 3, pp. 226–260, Weiss et al., Eds., Cold Spring Harbor Labortory, 1984.

*Primary Examiner*—David Guzo
*Attorney, Agent, or Firm*—McDonnell, Boehnen, Hulbert & Berghoff

[57] ABSTRACT

The present invention pertains to retroviral vector particles having target cell specificity which comprises a retroviral vector having a targeting peptide fused to the envelope protein of the retroviral vector to form a targeting envelope, wherein the targeting peptide replaces or disrupts the natural viral receptor binding site and the targeting peptide is the antigen binding site of an antibody, the receptor binding peptide of another virus, or is a peptide that specifically binds to a specific receptor of the target.

5 Claims, 6 Drawing Sheets

FIG. 2A pSNV-env-mC

FIG. 2B pSNV-env-mD

FIG. 2C pTC4

FIG. 2D pTC5

FIG. 2E pJD214 HV

FIG. 3

| | | | |
|---|---|---|---|
| ACTGGAGGCT | GATTTTGAA | GAAAGGGGTT | GTAGCCTAAA | AGATGATGGT |
| GTTAAGTCTT | CTGTACCTGT | TGACAGCCCT | TCCGGGTATC | CTGTCAGAGG |
| TGCAGCTTCA | GGAGTCAGGA | CCTAGCCTCG | TGAAACCTTC | TCTGACTCTG |
| TCCCTCACCT | GTTCTGTCAC | TGGCGACTCC | ATCACCAGTG | GTTACTGGAA |
| CTGGATCCGG | AAATTCCCAG | GGAATAAACT | TGAGTACATG | GGGTACATAA |
| GCTACAGTGG | TAGCACTTAC | TACAATCCAT | CTCTCAAAAG | TCGAATCTCC |
| ATCACTCGAG | ACACATCCAA | GAACCAGTAC | TACCTGCAGT | TGAATTCTGT |
| GACTACTGAG | GACACAGCCA | CATATTACTG | TGCAAGATAT | GGTGGTAACT |
| ATGCTATGGA | GTACTGGGGT | CAAGGAACCT | CAGTCACCGT | CTCCTCAGGA |
| GGTGGCGGTA | CAGGTGGCGG | AGGTACAGGC | GGAGGTGGTA | GAATTGTGAT |
| GACACAGTCT | CCATCCTCCC | TGGCTATGTC | AGTAGGACAG | AAGGTCACTA |
| TGAGCTGCAA | GTCCAGTCAG | AGCCTTTTAA | ATAGTAGCAA | TCAAAAGAAC |
| TATTTGGCCT | GGTACCAGCA | GAAACCAGGA | CAGTCTCCTA | AACTTCTGGT |
| ATACTTTGCA | TCCACTAGGG | AATCTGGGGT | CCCTGATCGC | TTCATAGGCA |
| GTGGATCTGG | GACAGATTTC | ACTCTTACCA | TCAGCAGTGT | GCAGGCTGAA |
| GACCTGGCAG | ATTACTTCTG | TCAGCAACAT | TATAGCACTC | CGTGGACGTT |
| CGGTGGAGGC | ACCAAGCTGG | AAATCAAACG | GGCTGA | |

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 836 base pairs
        ( B ) TYPE: nucleic acid
        ( C ) STRANDEDNESS: unknown
        ( D ) TOPOLOGY: unknown     ( i i ) MOLECULE TYPE: DNA (genomic)

( x i ) SEQUENCE DESCRIPTION: SEQ ID NO:1:

```
ACTGGAGGCT    GATTTTTGAA    GAAAGGGGTT    GTAGCCTAAA    AGATGATGGT    GTTAAGTCTT        60

CTGTACCTGT    TGACAGCCCT    TCCGGGTATC    CTGTCAGAGG    TGCAGCTTCA    GGAGTCAGGA       120

CCTAGCCTCG    TGAAACCTTC    TCTGACTCTG    TCCCTCACCT    GTTCTGTCAC    TGGCGACTCC       180

ATCACCAGTG    GTTACTGGAA    CTGGATCCGG    AAATTCCCAG    GGAATAAACT    TGAGTACATG       240
```

```
GGGTACATAA   GCTACAGTGG   TAGCACTTAC   TACAATCCAT   CTCTCAAAAG   TCGAATCTCC        300

ATCACTCGAG   ACACATCCAA   GAACCAGTAC   TACCTGCAGT   TGAATTCTGT   GACTACTGAG        360

GACACAGCCA   CATATTACTG   TGCAAGATAT   GGTGGTAACT   ATGCTATGGA   GTACTGGGGT        420

CAAGGAACCT   CAGTCACCGT   CTCCTCAGGA   GGTGGCGGTA   CAGGTGGCGG   AGGTACAGGC        480

GGAGGTGGTA   GAATTGTGAT   GACACAGTCT   CCATCCTCCC   TGGCTATGTC   AGTAGGACAG        540

AAGGTCACTA   TGAGCTGCAA   GTCCAGTCAG   AGCCTTTTAA   ATAGTAGCAA   TCAAAAGAAC        600

TATTTGGCCT   GGTACCAGCA   GAAACCAGGA   CAGTCTCCTA   AACTTCTGGT   ATACTTTGCA        660

TCCACTAGGG   AATCTGGGGT   CCCTGATCGC   TTCATAGGCA   GTGGATCTGG   GACAGATTTC        720

ACTCTTACCA   TCAGCAGTGT   GCAGGCTGAA   GACCTGGCAG   ATTACTTCTG   TCAGCAACAT        780

TATAGCACTC   CGTGGACGTT   CGGTGGAGGC   ACCAAGCTGG   AAATCAAACG   GGCTGA            836
```

( 2 ) INFORMATION FOR SEQ ID NO:2:

( i ) SEQUENCE CHARACTERISTICS:
        ( A ) LENGTH: 220 base pairs
        ( B ) TYPE: nucleic acid
        ( C ) STRANDEDNESS: unknown
        ( D ) TOPOLOGY: unknown     ( i i ) MOLECULE TYPE: DNA (genomic)

( x i ) SEQUENCE DESCRIPTION: SEQ ID NO:2:

```
GAGCTCCACC   GCGGTAAAGG   TCGCTGGGAA   GACCCCGTGG   ATCCACCACT   CTCGACTCAA         60

GAAAGCTCCT   GACAACCAAG   AAGAATGGAC   TGTCTCACCA   ACCTCCGATC   CGCTGAGGGT        120

AAAGTTGACC   AGGCGAGCAA   AATCCTAATT   CTCCTTGTGG   CTTGGTGGGG   GTTTGGGACC        180

ACTGCCGAAG   TTTCGCGAAG   GCCTTAAGTG   ACTAGGTACC                                  220
```

( 2 ) INFORMATION FOR SEQ ID NO:3:

( i ) SEQUENCE CHARACTERISTICS:
        ( A ) LENGTH: 40 amino acids
        ( B ) TYPE: amino acid
        ( C ) STRANDEDNESS: unknown
        ( D ) TOPOLOGY: unknown     ( i i ) MOLECULE TYPE:

( x i ) SEQUENCE DESCRIPTION: SEQ ID NO:3:

```
Met   Asp   Cys   Leu   Thr   Asn   Leu   Arg   Ser   Ala   Glu   Gly   Lys   Val   Asp   Gln
 1                       5                             10                            15

Ala   Ser   Lys   Ile   Leu   Ile   Leu   Leu   Val   Ala   Trp   Trp   Gly   Phe   Gly   Thr
                  20                            25                            30

Thr   Ala   Glu   Val   Ser   Arg   Arg   Pro
            35                      40
```

( 2 ) INFORMATION FOR SEQ ID NO:4:

( i ) SEQUENCE CHARACTERISTICS:
        ( A ) LENGTH: 28 base pairs
        ( B ) TYPE: nucleic acid
        ( C ) STRANDEDNESS: unknown
        ( D ) TOPOLOGY: unknown     ( i i ) MOLECULE TYPE: DNA (genomic)

( x i ) SEQUENCE DESCRIPTION: SEQ ID NO:4:

```
GGAGCGCTGA   CGTCGTGATG   ACCCAGTC                                                  28
```

( 2 ) INFORMATION FOR SEQ ID NO:5:

( i ) SEQUENCE CHARACTERISTICS:
        ( A ) LENGTH: 37 base pairs
        ( B ) TYPE: nucleic acid
        ( C ) STRANDEDNESS: unknown
        ( D ) TOPOLOGY: unknown     ( i i ) MOLECULE TYPE: DNA (genomic)

( x i ) SEQUENCE DESCRIPTION: SEQ ID NO:5:

CCTCGCGATC CACCGCCGGA GACTGTGAGA GTGGTGC        3 7

CELL TYPE SPECIFIC GENE TRANSFER USING RETROVIRAL VECTORS CONTAINING ANTIBODY-ENVELOPE FUSION PROTEINS AND WILD-TYPE ENVELOPE FUSION PROTEINS

BACKGROUND OF THE INVENTION

This application is a continuation of U.S. Ser. No. 08/205,980, filed Mar. 4, 1994, now abandoned, which is a continuation-in-part of U.S. Ser. No. 07/979,619, filed Nov. 20, 1992, now abandoned.

FIELD OF THE INVENTION

This invention relates to retroviral vector particles having target cell specificity. The retroviral vector particles comprise a retroviral vector having a chimeric envelope protein consisting of an antigen binding site of an antibody or another peptide fused to the envelope protein of the retroviral vector. The antigen binding site or the other peptide replaces or disrupts the natural viral receptor binding site. The resulting chimeric envelope is referred to as the "targeting envelope". This invention relates to retroviral vectors that contain not only the targeting envelope but also wild-type envelope protein. The presence of wild-type envelope in addition to the targeting envelope acts as a helper molecule by supplying a fully functional membrane fusion domain which may be impaired in targeting envelopes. This helper function enables and/or enhances infection of cells that do not contain a receptor for the wild-type envelope but do contain a receptor for the binding of the targeting molecule. This invention also relates to a method for preparing the retroviral particles and for using the retroviral vectors to introduce genes into vertebrate cells.

DESCRIPTION OF THE BACKGROUND

The disclosures referred to herein to illustrate the background of the invention and to provide additional detail with respect to its practice are incorporated herein by reference. For convenience, the disclosures are referenced in the following text and respectively grouped in the appended bibliography.

Retroviral vectors are the most efficient tools to introduce genes into vertebrate cells. Clinical experiments have been conducted to use retrovirus vectors to cure a genetic disease in humans (adenosine deaminase (ADA) deficiency). Besides correcting inborn errors of metabolism, gene therapy is also being tested in clinical trials to cure cancer and various other diseases (Science 1992, Vol. 258, pp. 744–746).

Retroviral vectors are basically retroviral particles that contain a genome in which all viral protein coding sequences have been replaced with the gene(s) of interest. As a result, such viruses cannot further replicate after one round of infection. Retroviral vector particles are produced by helper cells (FIG. 1). Such helper cells are cell lines that contain plasmid constructs which express all retroviral proteins necessary for replication. After transfection of the vector genome into such helper cells, the vector genome is encapsidated into virus particles (due the presence of specific encapsidation sequences). Virus particles are released from the helper cell carrying a genome containing only the gene(s) of interest (FIG. 1). In the last decade, several retroviral vector systems, derived from chicken or murine retroviruses, have been developed for the expression of various genes (for reviews see Temin, 1987; Gilboa, 1990).

Retroviral vectors have several limitations. Besides the limited genome size that can be encapsidated into viral particles, the most limiting factor for the application of retroviral vectors is the restricted host range of the vector particle. Some retroviruses can only infect cells of one species (ecotropic retroviruses) or even only one cell-type of one species (e.g., HIV). Other retroviruses have a very broad host range and can infect many different types of tissues of many different species (amphotropic retroviruses).

The initial step of retroviral infection is the binding of the viral envelope (env) glycoprotein to specific cell membrane receptors, the nature of which is unknown for most retroviruses. However, the interaction of the viral env protein with the cell surface receptor is very specific and determines cell-type specificity of a particular virus (Weiss et al, 1985). The envelope protein of all known retroviruses is made up of two associated peptides, (e.g., gp70 and p20(E) in SNV). These peptides are derived by proteolytic cleavage from the same precursor (gPR90env) encoded by the retroviral env gene. One peptide p20(E), also termed TM, anchors the protein in the membrane of the virus and, as shown with HIV, mediates the fusion of the virus and cell membranes. The second peptide gp70, also termed SU, mediates the binding of the virus to its receptor and, therefore, determines the host range (Weiss et al., 1985; Varmus and Brown, 1989).

Data obtained with several retroviruses indicate that the retroviral envelope protein forms trimers or tetramers. The formation of trimers appears to be mediated by the TM peptide (reviewed in Hunter, E. et al., 1990). Targeting envelopes retain TM in order to (i) maintain a membrane fusion function and (ii) maintain oligomerization. However, since X-ray pictures are not available, it is unclear whether or to what degree the construction of targeting-molecules impaired the structure of the membrane fusion domain.

BRIEF DESCRIPTION OF THE FIGURES

FIG. 1 (Parts A–C) is a diagram illustrating helper cells expressing retroviral proteins. A) Helper cells are made by the transfection of plasmids expressing all retroviral proteins necessary to form infectious virus particles. B) After transfection of the retroviral vector, the vector RNA genome is encapsidated into core structures. C) Helper cells that contain a plasmid express a modified envelope gene.

FIG. 2 (Parts A–E) is a diagram illustrating plasmids expressing mutant envelope genes of spleen necrosis virus (SNV).

FIG. 4 (Parts A–B) is a diagram illustrating helper cells expressing targeting envelopes plus wild-type envelopes. Such helper cells are made by the transfection of plasmids expressing the corresponding proteins. A) A helper cell expressing all retroviral proteins necessary to form (a) retroviral core proteins and (b) targeting envelope. B) Helper cells that contain targeting plus wild-type envelope are made by transfecting plasmids expressing genes encoding such proteins. After transfection of the retroviral vector that has the gene of interest, the retroviral vector RNA genome is encapsidated into retroviral vector particles displaying the envelope.

SUMMARY OF THE INVENTION

The present invention pertains to a retroviral vector particle having defined target cell specificity mediated by the nature of the targeting envelope which can be a chimeric protein consisting of an antigen binding site of an antibody or another peptide that binds to a specific cell surface structure (e.g., the receptor binding domain of another virus) fused to carboxy terminal parts of the retroviral envelope protein. The targeting envelope mediates the first step of retroviral infection which is the binding of the virus to a specific cell-surface receptor. The present invention also pertains to retroviral particles that contain a wild-type envelope in addition to the targeting envelope. The presence of the wild-type envelope serves to act as a helper molecule to improve or supplement a functional membrane fusion domain. Using target cells that do not contain a receptor for the wild-type envelope (e.g., SNV is not infectious for human cells), the wild-type envelope is only involved in the second step of retroviral infection, which is the efficient fusion of the viral and the cellular membranes. The present invention also pertains to the construction of retroviral vector particles containing a wild-type envelope in addition to a targeting envelope which can compensate for the loss of infectivity observed with retroviral particles that contain targeting envelopes alone.

In one embodiment, the present invention pertains to a retroviral vector particle having target cell specificity which comprises a retroviral vector having a targeting peptide fused to the envelope protein of the retroviral vector to form a targeting envelope, wherein the targeting peptide replaces or disrupts the natural viral receptor binding site and the targeting peptide is the antigen binding site of an antibody, the receptor binding peptide of another virus, or is a peptide that specifically binds to a specific receptor of the target.

In another embodiment, the present invention pertains to a cell type specific method for introducing genes into vertebrate cells using retroviral vectors which comprises administering to the cells a retroviral vector particle having target cell specificity which comprises a retroviral vector having a targeting peptide fused to the envelope protein of the retroviral vector to form a targeting envelope, wherein the targeting peptide replaces or disrupts the natural viral receptor binding site and the targeting peptide is the antigen binding site of an antibody, the receptor binding peptide of another virus, or is a peptide that specifically binds to a specific receptor of the target.

In yet another embodiment, the present invention pertains to a method for preparing a retroviral vector particle having target cell specificity which comprises a retroviral vector having a targeting peptide fused to the envelope protein of the retroviral vector to form a targeting envelope, wherein the targeting peptide replaces or disrupts the natural viral receptor binding site and the targeting peptide is the antigen binding site of an antibody, the receptor binding peptide of another virus, or is a peptide that specifically binds to a specific receptor of the target, which comprises the steps of:

(a) providing a targeting peptide;

(b) replacing part of the envelope gene coding for the viral receptor binding site with the targeting peptide to form a chimeric envelope gene;

(c) cloning the chimeric envelope gene in a eucaryotic gene expression vector; and (d) transfecting the chimeric envelope expression plasmid, a retroviral core protein expression plasmid, and a selectable marker gene expression plasmids into eucaryotic cells.

DETAILED DESCRIPTION OF THE INVENTION

Targeting Envelope

This invention relates to retroviral vector particles having target cell specificity. The retroviral vector particles comprise a retroviral vector having a chimeric envelope protein consisting of an antigen binding site of an antibody or another peptide fused to the envelope protein of the retroviral vector. The antigen binding site or the other peptide replaces or disrupts the natural viral receptor binding site. The resulting chimeric envelope is referred to as the "targeting envelope". This invention relates to retroviral vectors that contain not only the targeting envelope but also wild-type envelope protein. The presence of wild-type envelope in addition to the targeting envelope acts as a helper molecule by supplying a fully functional membrane fusion domain which may be impaired in targeting envelopes. This helper function enables and/or enhances infection of cells that do not contain a receptor for the wild-type envelope but do contain a receptor for the binding of the targeting molecule. This invention also relates to a method for preparing the retroviral particles and for using the retroviral vectors to introduce genes into vertebrate cells.

To alter the host range of a vector particle, retroviral vector particles may be constructed that contain modified envelope proteins that recognize only a cell surface structure (receptor) specific for the target cell of interest. Proteins known to recognize specific structures of proteins are antibody molecules. Hence, to make a retroviral vector particle specific for a cell-type of interest, the viral receptor binding peptide may be replaced with an antigen binding site of an antibody molecule. To test whether vector particles containing such antigen binding sites are competent for infection, model systems were developed using an antigen binding peptide of an antibody against the hapten dinitrophenol (DNP) fused to envelope gene of spleen necrosis virus (SNV).

The use of the anti-hapten (anti-DNP) antibody has many advantages. (1) The interaction of this antigen with the antibody is well characterized (Davies and Metzger, 1983). (2) The hapten is easily available. (3) A large variety of cells (which cannot be infected with wild-type vector particles) can be conjugated with this hapten. DNP conjugated cells bind antibodies directed against this hapten. Thus, the hapten may mimic the (abundant) presence of a receptor for the chimeric vector particle. (4) Anti-hapten antibodies are frequently internalized by the cell. Thus, in the case, the construction of chimeric envelope proteins will destroy the membrane fusion domain of TM, this property may compensate for this loss of function. (5) An in vitro binding assay can be easily established to test for virus particle formation and binding of such viruses to DNP.

Wild-Type Envelope

This invention relates to retroviral particles having a target cell specificity. The retroviral vector particles comprise a retroviral vector having a targeting envelope which mediates the binding of the retroviral vector particle to a cell surface receptor of the target cell. This binding is very specific and determines the host range and cell-type specificity. The particles also have a wild type envelope. Using target cells that do not contain a viable receptor for the wild type envelope, the function of the wild-type envelope is only to supply a fully functional membrane fusion domain. This invention also relates to the method for preparing the retroviral vector particles and a method for using the retroviral vectors to introduce genes into vertebrate cells.

Retroviral vectors derived from spleen necrosis virus containing wild-type envelope alone cannot infect human or hamster cells. In these infectivity studies, retroviral particles harvested from DSN cells were used (Dougherty, J. P. and Temin, H. M. 1989) to infect human HeLa and Col-1, as well as hamster CHTG (ret. 1) cells (Tables 1 and 2). DSN cells are standard retroviral packaging cells containing a plasmid expressing the retroviral core proteins and another plasmid expressing wild-type envelope (Dougherty, J. P. and Temin, H. M., 1989).

To introduce genes into such cells using SNV retroviral vector particles, two different approaches were made using different targeting envelopes in combination with and without additional wild-type envelope.

Figure 4A:
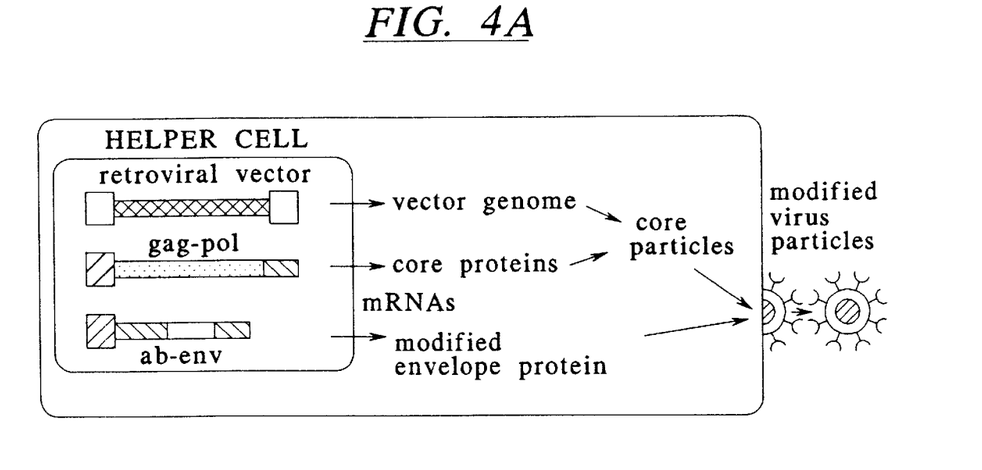
Figure 4B:
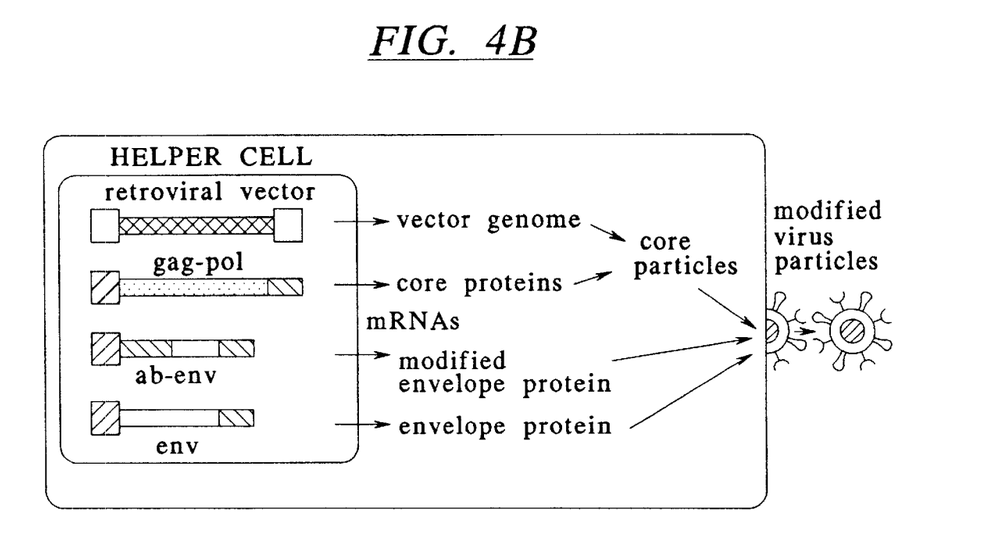

1. Targeting of human cancer cells (HeLa and Col-1) with SNV retroviral vectors. The antigen binding site of an antibody directed against the hapten DNP was used. However, the antigen binding site used in the targeting envelope was derived from an antibody (termed B6.2, Bird, R. E. et al., 1988 and Colcher, D. et al., 1990) directed against a cell-surface protein expressed on various human cancers (e.g. HeLa and Col-1 cells, Bird, R. E. et al., 1988 and Colcher, D. et al., 1990). The gene constructs (FIG. 6) for the expression of the targeting envelope are similar to that described above. In particular, in two constructs (FIG. 6, pTC24 and pTC25), the antibody moiety was fused to exactly the same position of the SNV envelope gene as the anti-DNP antibody described below (for more details, see below: Material and Methods). To test, whether the addition of a fully functional membrane fusion domain (provided by wild-type envelope) would increase the efficiency of infection, helper cells expressing retroviral core proteins, wild-type envelope, and the targeting envelope were developed (FIG. 4). Virus was harvested from such helper cells and subjected to infectivity studies.

2. Targeting CHTG cells that express a receptor for ecotropic murine leukemia virus. To test whether retroviral particles derived from SNV displaying targeting molecules other than antigen binding sites of an antibody are infectious, targeting envelopes were constructed that contained the receptor binding peptide of another virus (murine leukemia virus) fused to the envelope of SNV. Infectivity of virus particles displaying such targeting envelopes with and without wild-type envelope was tested.

EXAMPLES

Targeting Envelope

Materials and Methods

Construction of Antibody-Envelope Fusion Genes

The gene coding for the envelope protein of spleen necrosis virus (SNV) does not contain suitable restriction enzyme sites to enable the construction of antibody-envelope fusion genes. Thus, point mutations were introduced (by site directed mutagenesis) in the SNV env gene at different locations to create restriction enzyme recognition sites. For this purpose, the SNV env gene (HindIII-SacI fragment) was subcloned into pSelect (a vector specifically designed for site directed mutagenesis). Restriction sites for enzymes that create blunt ends were introduced in such a way that the restriction enzymes cut between two codons. Following consistently this strategy, all mutants can be used to create deletions, insertions, and fusions in any combination without altering the reading frame. Further, restriction enzyme sites were nested between regions coding for hydrophobic and hydrophilic domains. It was hypothesized that the deletion of a certain domain(s) would not interfere with the proper folding of the following domain. This hypothesis is based on the finding that many proteins in evolution arose by exon shuffling of functional domains.

Some mutant envelopes that have been made are shown in FIG. 2. pSNV-env-mC (FIG. 2a) contains a new restriction enzyme site located between a hydrophobic and a hydrophilic peptide domain. In this mutant, the change in the nucleotide sequence does not alter the amino acid sequence. Thus, pSNV-env-mC can be considered as a positive control. pSNV-env-mD contains a new restriction enzyme site within the cleavage site of the envelope precursor. The introduction of the mutation also altered the amino acid sequence destroying the common motive found in all cleavage sites of all retroviruses investigated. Thus, it was expected that the resulting envelope precursor would not be cleaved, and, therefore, would not to give rise to infectious virus particles. Mutated env genes were inserted into pHB3, a eucaryotic gene expression vector (FIG. 2).

Figure 2A:
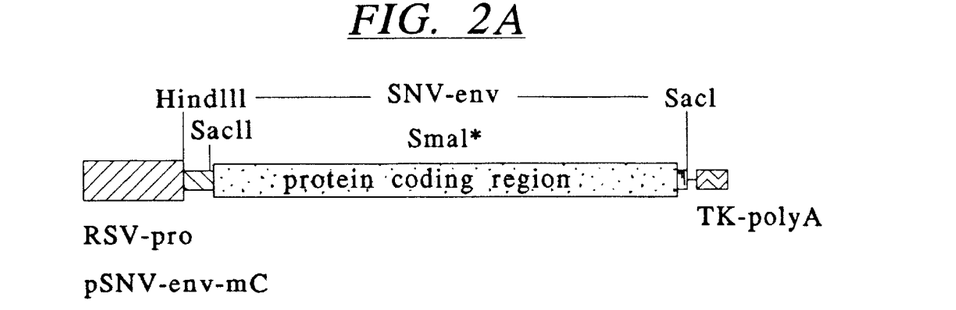
Figure 2B:
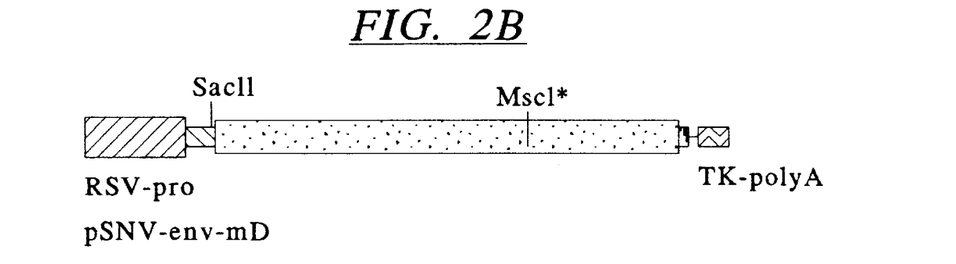
Figure 2C:
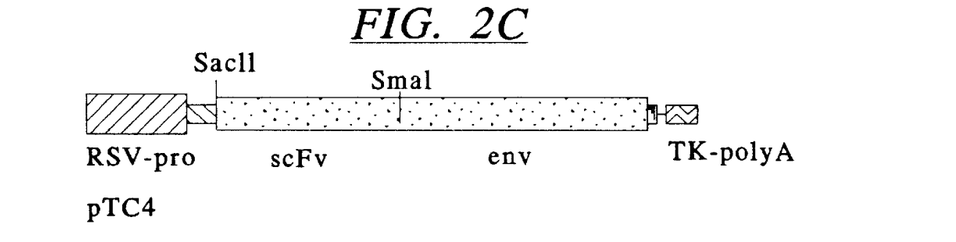
Figure 2D:
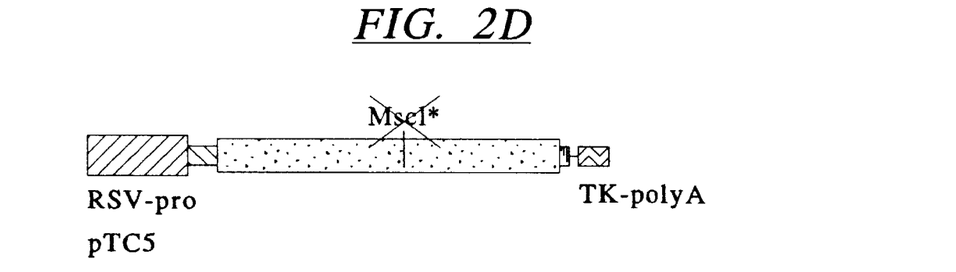
Figure 2E:
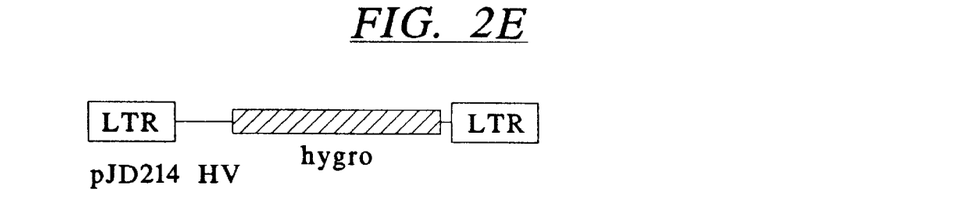
Figure 3:
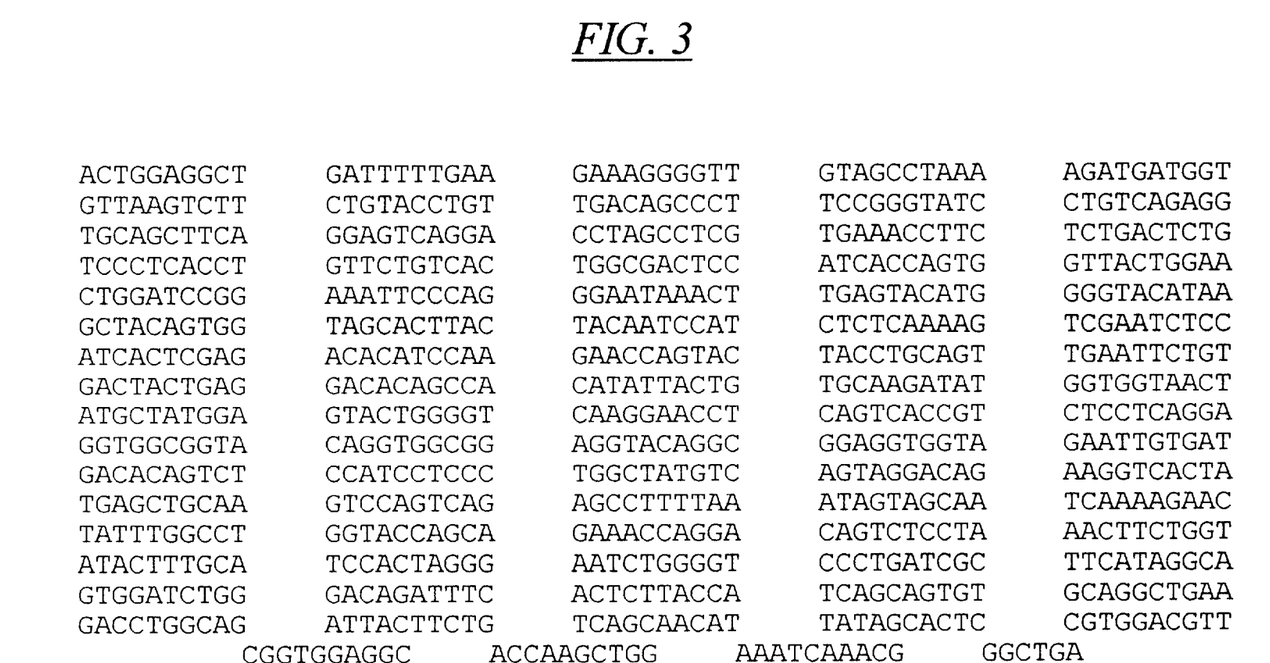
FIG. 3 shows the sequence of the single chain antibody gene (scFv) against the hapten DNP.

The genes coding for the heavy and the light chain of an antibody against DNP have been kindly provided by Dr. Ogawa (Scripps Clinic, La Jolla, Calif.). The genes were sequenced and published (Riley et al., 1986). Using PCR technology as described (Whitlow and Filpula, 1990), a single chain antibody gene was constructed including the signal peptide against DNP. The PCR product was cloned into the SmaI site of pBluescript. DNA sequencing confirmed the successful combination of the two gene segments coding for the variable regions of the antigen binding peptide. The complete sequence of the anti-DNP scFv gene is given in FIG. 3. A SacII (located in the polylinker of pBluescript) to SmaI (located in the 3' PCR primer) fragment was inserted into eucaryotic expression vectors replacing amino terminal parts of the envelope gene as follows: in pTC4, the SacI (located upstream of the ATG codon of the env gene) to SmaI fragment of env was replaced with the scFv gene; in pTC5 the SacII to the MscI fragment of env was replaced with the scFv gene (FIG. 2C and 2D, respectively). After cloning, the antibody-envelope junctions were sequenced to verify the maintenance of the correct reading frame of the chimeric gene.

In vitro Binding Assays

The in vitro binding assays were performed in the following manner. DNP was conjugated to BSA (DNP-BSA was used to raise the initial antibodies from which the scFv genes have been derived). DNP-BSA was coupled to activated Sepharose following the protocol recommended by the supplier (Sigma). An Elisa assay with a anti-DNP antibody (kindly provided by Dr. S. Pestka) confirmed the successful coupling reaction. 100 ml of tissue culture supernatant medium was incubated with 50 ml of DNP-BSA-Sepharose for 30 minutes at 37° C. After incubation, the sepharose particles were pelleted by centrifugation in a Qualitron minicentrifuge for 30 seconds. The pellets were rinsed once with PBS. The PBS was removed and reverse transcription assays were performed by adding the reaction to the sepharose pellet. The reverse transcription assay was done using standard procedures; incorporation of 32PdTTP into cDNA was determined by TCA precipitation as described (Schleif and Wensink, 1981).

Test for Infectivity of Particles Containing Antibody-Envelope Fusion Proteins

The envelope expression plasmids shown in FIG. 2 were transfected into D17 cells (a dog osteosarcoma cell-line) in cotransfection with pBR1 and pJD214HY (FIG. 2), plasmids expressing the retroviral core proteins, and containing a retroviral vector for the expression of the hygromycin phosphotransferase gene, respectively (see also FIG. 1). Cells were selected for hygromycin resistance. After selection for hygromycin resistance, virus was harvested from confluent cell cultures and infectivity assays were performed (see below). Infected target cells were selected for hygromycin resistance (D17 cells were incubated with medium containing 60 mg/ml hygromycin, CHO cells with medium containing 250 mg/ml hygromycin). Hygromycin resistant cell colonies indicate infectious virus particles.

Infectivity assays were performed on D17 and CHO cells with and without conjugated DNP. DNP was conjugated to cells as follows: Cells were incubated with 500 ml of a solution containing 1.4 mg/ml DNBS (2,4,-Dinitrobenzene-sulfonic acid, 2-hydrate, purchased from Kodak) in sodium cocodylate buffer (0.25M) for 3 to 5 minutes at room temperature. The conjugation reaction was stopped by adding 5 ml of medium to the cells.

Infections of non-conjugated cells were performed in the presence of 50 mM polybrene using standard protocols. In the case of DNP conjugated cells, infection was performed without polybrene.

Wild-Type Envelope

Material and Methods scA Targeting Vectors

To construct a targeting envelope containing the antigen binding site of an antibody directed against a cell-surface protein expressed on several human tumor cells, the corresponding single chain antibody gene (termed B6.2, Bird, R. E. et al., 1988 and Colcher, D. et al., 1990) made for expression in *E. coli.* was modified in the following way: PCR technology was used to amplify the B6.2 scA gene using the original *E. coli.* expression plasmid as template (Bird, R. E. et al., 1988 and Colcher, D. et al., 1990). The primers used had the following sequence:

primer A: 5' GGAGCGCTGACGTCGTGATGACCCAGTC 3'
(SEQ ID NO:4)

primer B: 5' CCTCGCGATCCACCGCCGGAGACTGT-
GAGAGTGGTGC3' (SEQ ID NO:5)

Figure 5:
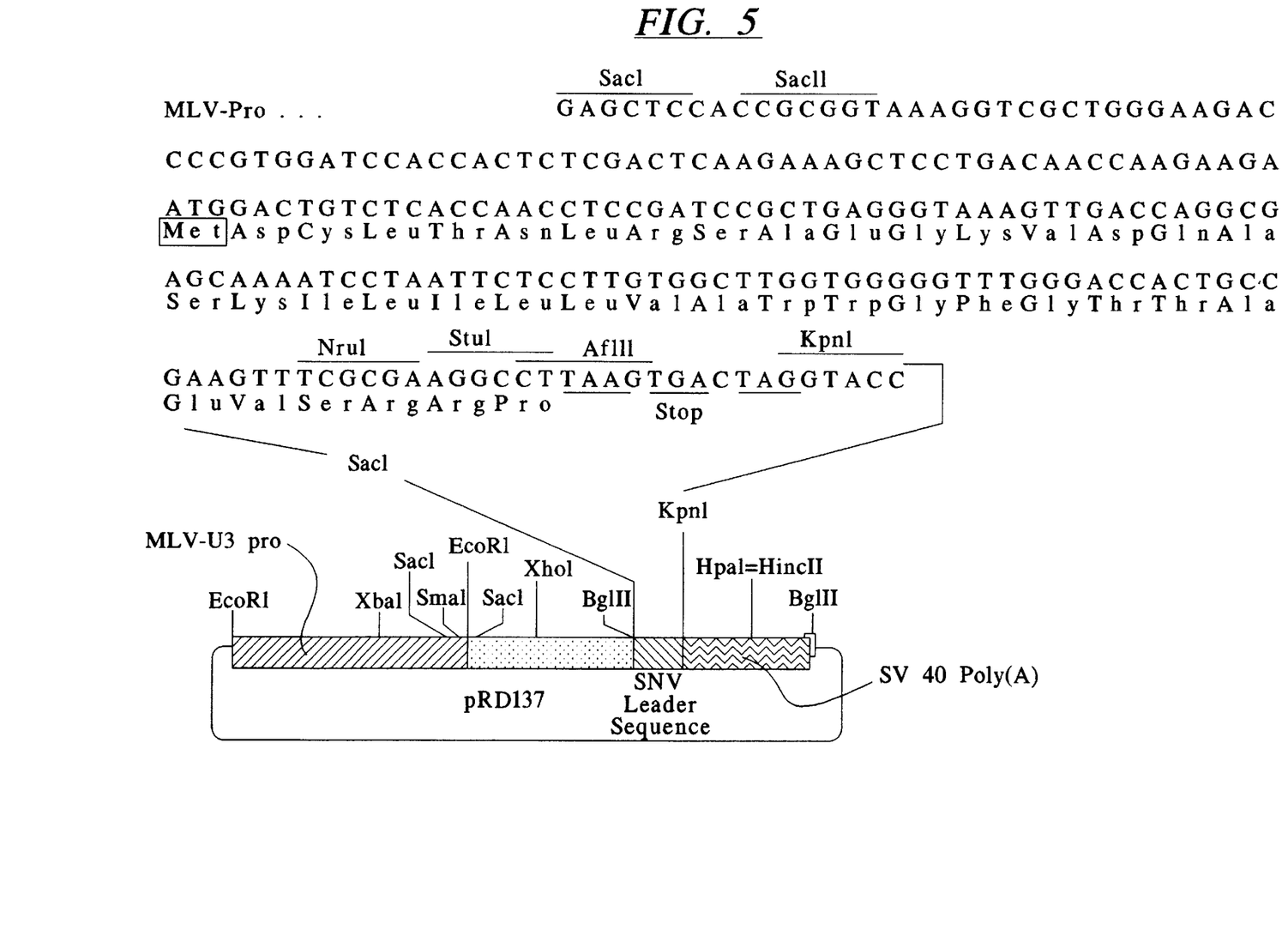
FIG. 5 is a diagram of a eucaryotic gene expression vector constructed. The gene expression vector was derived from a similar vector described recently (Sheay, W. et al., 1993).
Figure 6:
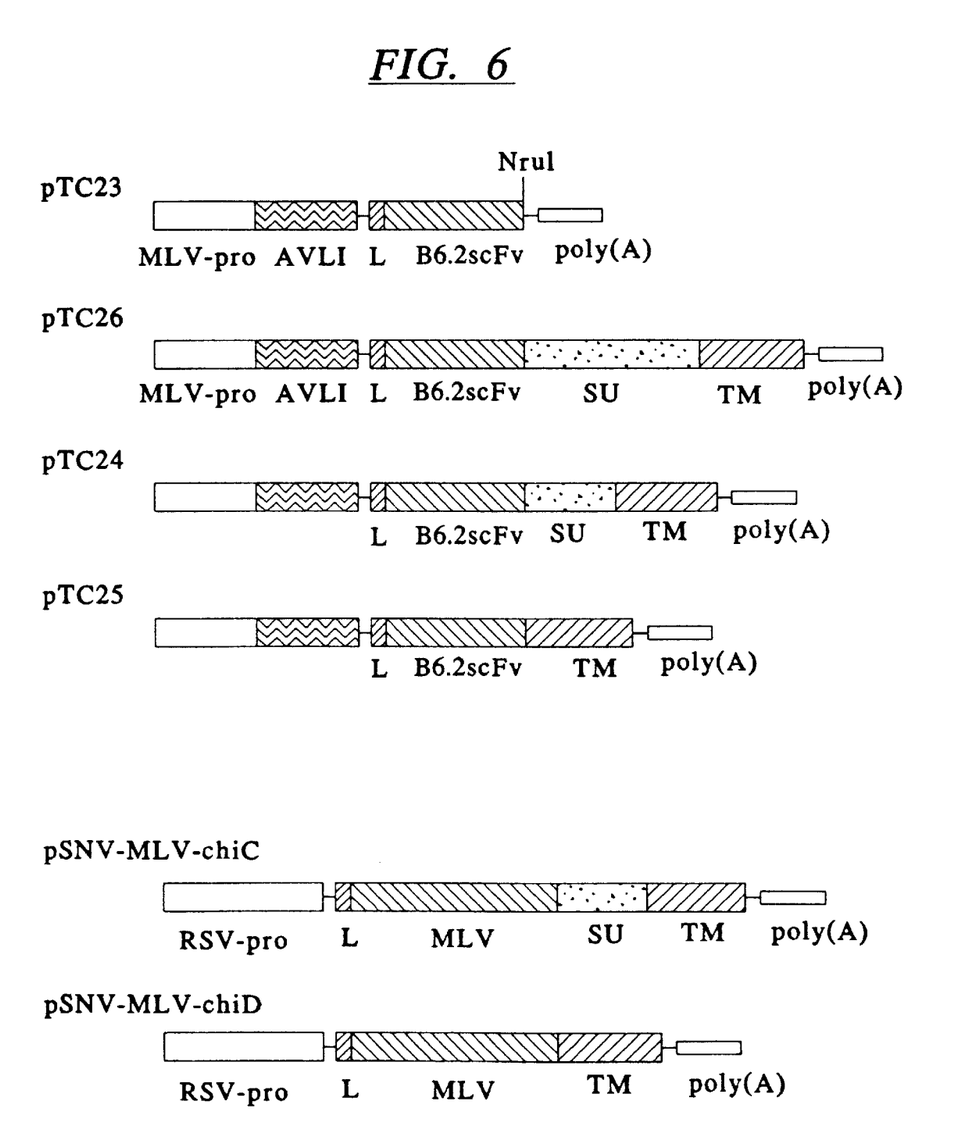
FIG. 6 is a diagram illustrating plasmids expressing spleen necrosis virus, SNV, core structure proteins, wild-type envelope proteins, and various targeting envelope proteins.

The PCR amplification results in a fragment that does not contain the bacterial ompA signal sequence and the stop codons present in the original B6.2 gene (Bird, R. E. et al., 1988 and Colcher, D. et al., 1990). The PCR products were cloned into the SmaI site of the pBluescript vector (Stratagene) and sequenced to verify a correct reading frame. The plasmid was termed pTC9. The B6.2 gene was isolated by digesting the pTC9 plasmid with Eco47III plus NruI. The corresponding restriction enzyme recognition sites have been introduced with the primers used for PCR amplification. The B6.2 gene (the Eco47III to NruI fragment was cloned into pTC13, a gene expression vector (FIG. 5). The corresponding vector (termed pTC23) contains the ER transport signal sequence of the SNV envelope protein fused to the B6.2 gene to enable transport through the endoplasmatic reticulum. The cloning reconstituted the NruI site at the 3' end of the B6.2 gene. Carboxy terminal parts of the SNV envelope gene were isolated and fused to the B.2 gene (NruI site) to give plasmids pTC24, pTC25, and pTG26 (FIG. 6). Plasmids pTC24 and pTC25 retain exactly the same portions of the retroviral envelope as plasmids pTC4 and pTC5 which contain the anti-DNP antibody. In plasmid pTC26, the antibody is fused to codon 168 of the SNV envelope.

Chimeric SNV-MLV targeting envelope

Targeting envelopes containing the receptor binding peptide of another virus were made as follows: the gene segment of ecotropic murine leukemia virus (a HindIII-BalI fragment comprising almost the complete region coding for the SU peptide, including its ER transport signal sequence, Ott, D., and Rein, A. 1992) was isolated and inserted into the vectors pSNV-env-mC and pSNV-env-mD (pSNV-env-mC and pSNV-env-mD was described in FIG. 2) replacing the amino terminal parts of the SNV envelope gene. The resulting constructs are identical to plasmids pTC4 and pTC5, respectively, except that the anti-DNP antibody peptide (anti-DNP scA) is replaced by the receptor binding peptide of ecoMLV (FIG. 6, pSNV-MLV-chiC and pSNV-MLV-chi-D, respectively).

Experimental system

Briefly, helper cells were made as described above by transfecting plasmids expressing retroviral gag-pol proteins, the retroviral targeting envelope, and the wild-type envelope into D17 cells in co-transfection with a selectable marker to obtain helper cell lines containing targeting envelope only or helper cells containing both targeting and wild-type envelope. Infectivity assays were performed on a variety of different cell-lines which included D17 cells, CHTG-cells expressing the ecotropic murine leukemia virus receptor (Albritton, L. M. et al., 1989) and human HeLa and Col-1 cells. Infectivity was determined with a retroviral vector expressing the bacterial beta-galactosidase gene as described (Mikawa, T. et al.).

RESULTS

Targeting Envelope

In vitro binding assay. The in vitro binding assays showed that only cells transfected with pSNV-env-mD produce viral vector particles that contain a chimeric envelope able to bind DNP (see also Table 1).

Infectivity studies. The results of the infectivity experiments are summarized in Table 1. Vector particles containing wild-type envelope (pSNV-env-mC) infected D17 cells with an efficiency of about 105 colony forming units per ml of tissue culture supernatant medium. Such virus particles also infected D17 cells conjugated with DNP. However, the efficiency of infection was three orders of magnitude less than that of cells not conjugated with DNP. This drop in virus titer is mainly due to difficulties of selecting DNP conjugated cells with the antibiotic. It appears that the conjugation reaction makes cells very vulnerable to the drug and more than 90% of the cells died two to three days after the conjugation reaction. Virus particles with wild-type envelope do not infect CHO cells.

The mutation of the cleavage site of the envelope precursor protein (SNV-env-mD) completely abolished infectivity. Only one colony was observed in D17 cells not conjugated with DNP. This finding coincides with earlier reports that mutations in the envelope precursor cleavage site lead to non-infectious virus particles. Cells transfected with pTC4 (FIG. 2) did not produce vector particles that were able to infect D17 or CHO cells at significant efficiencies. Cells transfected with pTC5 produced virus particles unable to infect D17 or CHO cells. However, such particles significantly infected cells conjugated with DNP.

Wild-Type Envelope

First, the presence of wild-type envelope in particles displaying an antigen binding site against DNP was tested to determine whether there would be an increase in the efficiency of infection of cells conjugated with DNP. It was found that DNP conjugated HeLa cells could not be infected with vector virus particles that contained the wild type envelope alone. However, DNP conjugated cells could be infected with anti-DNP displaying retroviral vectors at a very low efficiency. The titer measured was about 10 infectious units per ml of tissue culture supernatant medium. Virus particles that contained wild-type envelope in addition to the targeting anti-DNP envelope infected cells 10 to 30 times more efficiently. This data indicate that the presence of wild-type envelope can increase the efficiency of infection of targeting vectors. Two additional sets of experiments using other targeting molecules were performed to corroborate this finding.

1. Infectivity studies with virus particles containing antibody-envelope fusion proteins. D17 cells, HeLa cells and Col-1 cells were infected with virus particles displaying an antigen binding site of an antibody (B6.2, Bird, R. E. et al., 1988 and Colcher, D. et al., 1990) directed against a cell surface protein expressed on various human carcinoma cells. Vector virus particles were harvested from a variety of different helper cell lines (Table 2). All virus particles were carrying a vector transducing the bacterial beta-galactosidase gene. Infectivity was determined by staining the cells with X-gal as described (Mikawa, T. et al.). The number of blue cell colonies was determined two to three days after infection. The following virus particles were tested for infectivity: virus particles that do not contain envelope (termed "no env"), virus particles that contain wild-type envelope alone (termed wt-env-DSN), virus particles that contain targeting envelopes alone which are antibody-envelope fusion proteins (termed TC24, TC25, and TC26 as described in FIG. 6), and particles that contain wild-type plus targeting envelopes (termed TC24+wt-env, TC25+wt-env, and TC26+wt-env).

Particles that do not contain any envelope were found to be basically not infectious. Particles that contain wild-type envelope were infectious only on D17 cells which contain a viable receptor for wild-type SNV. The particles were not infectious on HeLa cells or Col-1 cells. Particles that contained targeting envelopes only were infectious on D17 and HeLa cells. The efficiency of infection on D17 cells was less than 5% of that of virus containing wild-type envelope. Such particles were not infectious on Col-1 cells. The addition of wild-type envelope increased efficiency of infection 10 to 50 fold. Further, Col-1 cells that could not be infected with particles containing either envelope alone could be infected with particles containing both wild-type env and targeting env. This data indicates that the wild-type envelope adds a function improving or even completely enabling virus penetration (Table 2). These data also show that the level of infectivity is dependent on the position within the envelope gene at which the antibody is fused to the envelope.

2. Infectivity studies with virus particles containing SNV-MLV-fusion proteins. CHTG cells (described in Albritton, L. M. et al., 1989) expressing the receptor of ecotropic murine leukemia virus as well as D17 cells were infected with virus harvested from cells expressing targeting envelopes (SNV-MLV-chi-C and SNVMLV-chi-D) alone or from helper cells expressing targeting envelope plus wildtype envelope. Virus particles were carrying the hygromycin B resistance gene. Infected cells were selected for hygromycin resistance and the number of hygromycin resistant cell colonies was determined. Retroviral vector particles containing the targeting envelope alone were not infectious. The particles became infectious after wild-type envelope was added to the particles. Particles with wild-type envelope alone are not infectious on CHTG cells (Table 3).

DISCUSSION

Targeting Envelope

The data obtained with retroviral particles containing antibody-envelope fusion proteins showed that such particles are competent for infection. Surprisingly, TC4, a construct that contains the scFv gene fused to env in the middle of SU did not give virus particles capable of binding DNP. This may be due to an unstable SU-TM complex. This hypothesis is supported by the finding that such particles failed to bind to DNP-BSA-Sepharose. Low level infectivity of such particles on D17 cells may result from unspecific adsorption of virus particles containing TM only. Unspecifically adsorbed virus particles (depleted of SU) may occasional penetrate the cell.

Cells transfected with pTC5 produce virus particles with chimeric envelopes without a functional retroviral membrane fusion domain. This assumption is based on the finding that virus particles containing uncleaved envelope precursor proteins (SNV-env-mD) are not infectious. However, it is known that some antibody molecules are internalized by cells after binding to cell surface by an unknown mechanism. The data show that such an internalization mechanism might be sufficient to allow internalization of the virus particle and the consequent establishment of a successful infection.

Applications of Vector Particles With Antibody-Envelope Fusion Proteins in Gene Therapy In all applications of human gene therapy so far, the cells of interest were isolated from the patient, purified from other cell types, and infected in tissue culture with retroviral vector particles which were harvested from helper cells. After expansion of the treated cells in tissue culture, they were re-injected into the patient. The infection of cells has to be done in vitro, since the retroviral vector particles used (derived from amphotropic murine retroviruses) have a broad host range. Thus, if injected directly into the blood stream of a patient, such virus particles would infect all kinds of tissue. Besides other risks, this treatment would be inefficient, since the chance that the gene will be delivered to its appropriate target cell is very low.

This clinical gene therapy protocol may be sufficient to obtain insight into how efficient and how beneficiary gene therapy will be for the patient. Indeed, the clinical data look very promising (Eglitis, personal communication). However, the current clinical protocol is very laborious, time consuming, very costly, and, therefore, not suitable for general clinical application. For general clinical application, it will be necessary to inject the gene transfer vehicle directly into the body of the patient.

The development of a retroviral vector particle that only infects one specific cell type, may allow the direct injection of the vector into the patient's blood stream. The development of vector particles containing antibody-envelope chimeras may be the first step towards this goal and may open a new area of possible applications of gene therapy in vivo.

Wild-Type Envelope

Retroviral vector particles which display an antigen binding site of an antibody can specifically infect cells that contain a antigen specific for the antibody. However, the efficiency of the gene transfer can be low. We hypothesized that the fusion of the targeting peptide to the envelope impaired the natural fusion function of the envelope which is essential for efficient penetration of the virus. Thus, the hypothesis that the addition of a wild-type envelope may complement this shortcoming was tested.

New retroviral vector particles containing two different types of targeting envelopes were constructed. These targeting envelopes were: (1) fusion proteins containing the antigen binding site of an antibody fused to various carboxy terminal portions of the envelope protein of spleen necrosis virus, SNV; and (2) fusion proteins consisting of the receptor binding domain of ecoMLV fused to various carboxy terminal portions of the SNV, similar to the antibody envelope constructs (FIG. 6).

Targeting envelopes alone are little or not infectious on cells that contain a receptor for the targeting envelope. The addition of wild-type envelope to particles containing targeting envelopes dramatically increased or even completely enabled infectivity on target cells that could hardly or not at all infected with virus particles containing either envelope alone. This data show that the construction of particles containing mixed envelopes dramatically improves the efficiency of gene transfer into specific target cells and, therefore, provides a valuable tool to introduce genes into specific target cells.

This method can be probably be improved by mutating the natural receptor binding domain of the wild-type envelope (e.g., by site directed mutagenesis). Using a wild-type envelope containing a non-functional receptor binding site in mixed envelope retroviral vector particles may enable to also target cells that contain a receptor for the wildtype envelope without loosing target cell specificity.

TABLE 1

Infectivity of Retroviral Vector Particles on D17 and CHO Cells With and Without DNP Conjugation*

| Envelope of virus particle | Binding to DNP | Virus titer (cfu/ml) D17 cells | D17 + DNP | CHO − DNP | CHO + DNP |
|---|---|---|---|---|---|
| SNV-env-mC | nd | $10^5$ | $10^2$ | 0 | 0 |
| SNV-env-mD | − | 1 | 0 | 0 | 0 |
| TC4 | − | 10 | 0 | 0 | 1 |
| TC5 | + | 0 | $10^2$ | 0 | 10 |

*Virus was harvested from tissue culture cells expressing SNV gag-pol and the envelope protein indicated in the left column (see also FIG. 2). All cells contained pJD214HY, a retroviral vector expressing the hygromycin B phosphotransferase gene. Infected cells were selected for hygromycin resistance. The number of hygromycin resistant cell colonies was determined two to three weeks after infection (after all cells had died in uninfected control plates). DNP binding of vector particles was the determined by measuring reverse transcriptase activity bound to DNP-BSA-Sepharose particles. nd: not determined; 0: no hygromycin resistant colonies were detected. Virus titers are expressed as colony forming units (cfu) per ml of tissue culture supernatant medium.

TABLE 2

Infectivity of Retroviral Vector Particles Displaying The B6.2 Single Chain Antigen Binding Peptide

| Construct gag-pol + | Titer (CFU/ml) D17 | HeLa | COL-1 |
|---|---|---|---|
| no env | 1 | nd | —* |
| wt-env (DSN) | 1,000 | nd | nd |
| TC26 | 40 | 10 | nd |
| TC24 | 20 | 5 | nd |
| TC25 | 45 | 20 | nd |
| TC26 + wt-env | 1,100 | 90 | 45 |
| TC24 + wt-env | 10,000 | 250 | 115 |
| TC25 + wt-env | 4,000 | 100 | 55 |

Plasmid constructs pTC24, pTC25, and pTC26 were transfected into D17 cells that express retroviral core proteins (gag-pol) and the vector pCXL (Mikawa, T.), or into the retroviral packaging line DSN also containing the pCXL vector (in co-transfection with a plasmid expressing an antibiotic resistance gene). The pCXL vector transfers the bacterial, B-galactosidase (taco gene. Virus was harvested from stable transfected cell-lines and fresh D17 cells, HeLa cells, or Col-1 cells were infected. Two days after infection, cells were stained with X-gal. Blue cells indicate infected cells expressing the lacZgene. Virus titers are expressed as colony forming units per ml tissue culture supernatant medium harvested from helper cells (cfulml).
—* experiment not done.
nd: no infected cells were detected in infection experiments using a total of 2 ml supernatant tissue culture medium.

TABLE 3

Infectivity of Retroviral Vector Particles Containing Chimeric Envelope Proteins of MLV and SNV

| Envelope of virus particle cells | Virus titer (cfu/ml) D17 cells | CHTG |
|---|---|---|
| MLY-SNV-chiC | nd | nd |
| MLV-SNV-chiD | nd | nd |
| MLV-SNV-chiC + wt SNV | $10^6$ | $10^3$ |
| MLV-SNV-chiD + wt SNV | $10^6$ | $10^3$ |
| DSN | $10^5$ | nd |

Virus was harvested from tissue culture cells expressing SNV gag-pol and the envelope protein indicated in the left column (see also FIG. 6). All experiments were performed with pJD214HY a retroviral vector transferring the hygromycin resistance gene. Virus titers are expressed as hygromycin resistant colony forming units per ml of tissue culture supernatant medium. SNV-MLV-chiC + wt SNV and SNV-MLV-chiD + wt SNV are cell lines expressing chimeric envelopes of MLV and SNV plus the envelope of wild type (wt) SNV. DSN cells are SNV based helper cells expressing gag-pol and SNV env from two different plasmid constructs. Virus titers are expressed as colony forming units (cfu) per ml of tissue culture supernatant medium.
nd: no hygromycin resistant colonies were detected using a total of 5 ml tissue culture medium.

The term "oligonucleotide" as used herein refers to primers, probes, oligomer fragments to be detected, oligomer controls, and unlabeled blocking oligomers. Oligonucleotide are molecules comprised of two or more deoxyribonucleotides or ribonucleotides. The term "primer" as used herein refers to an oligonucleotide, preferably an oligodeoxyribonucleotide, either naturally occurring such as a purified restriction digest or synthetically produced, which is capable of acting as a point of initiation of synthesis when subjected to conditions in which synthesis of a primer extension product, which is complementary to a nucleic acid strand, is induced, i.e., in the presence of nucleotides, an agent for polymerization such as a DNA polymerase, and a suitable temperature and pH. The primer must be sufficiently long to prime the synthesis of extension products in the presence of the polymerization agent. Methods for amplifying and detecting nucleic acid sequences by polymerase chain reaction (PCR) are described in detail in U.S. Pat. Nos. 4,683,195, 4,683,202, and 4,965,188, which disclosures are incorporated herein by reference.

Figure 1A:
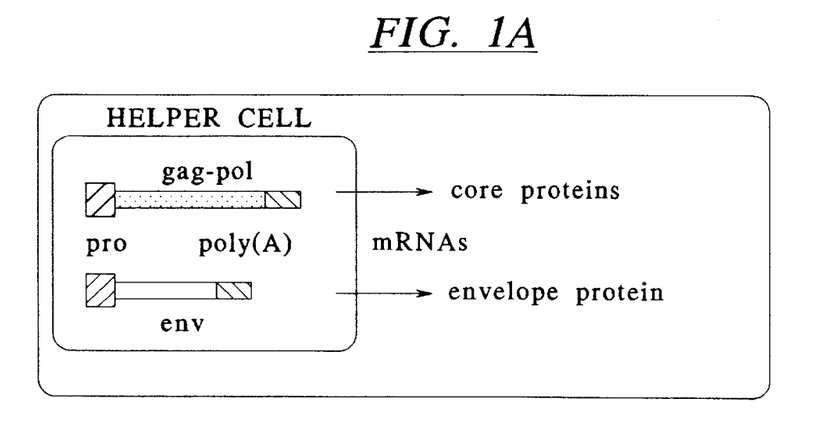
Figure 1B:
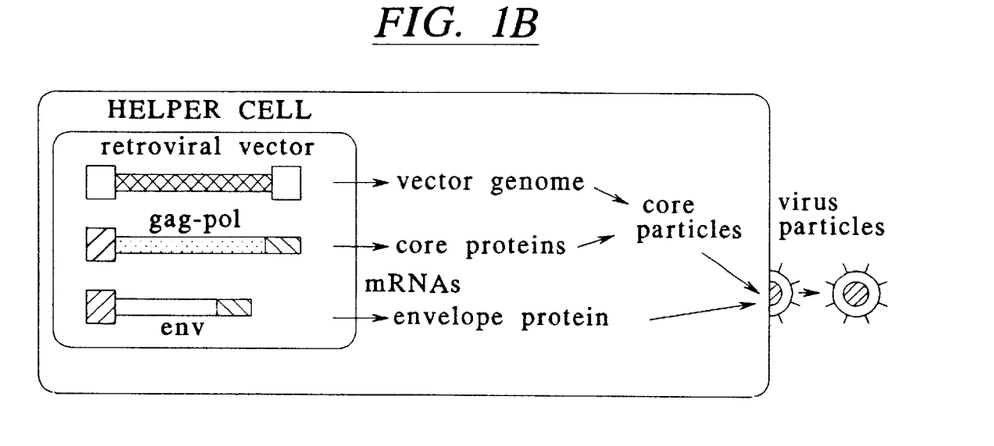
Figure 1C:
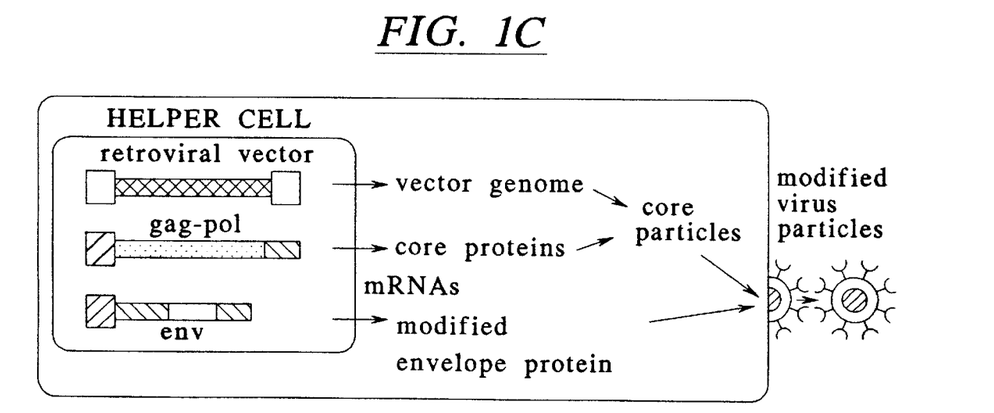

FIG. 1 is a diagram illustrating helper cells expressing retroviral proteins. A) Helper cells are made by the transfection of plasmids expressing all retroviral proteins necessary to form infectious virus particles. One plasmid is designed to express all core/proteins (expression of gag and pol). The other plasmid is designed to express the envelope precursor/protein. Both plasmid constructs do not contain retroviral cis/acting sequences for virus replication (e.g., encapsidation sequences, a primer binding site etc.). Polyadenylation takes place in non/retroviral polyadenylation recognition sequences. B) After transfection of the retroviral vector, the vector RNA genome is encapsidated into core structures. The helper cell is producing retroviral particles that only contain the vector genome with the gene(s) of interest. The vector contains all cis/acting sequences for replication. Thus, in infected target cells, the vector genome is reverse transcribed and integrated into the genome. Due to the lack of retroviral protein coding genes in the vector genome, no virus particles are produced from infected target cells. C) Helper cells that contain a plasmid express a modified envelope gene. The helper cell is very similar to that shown above. However, chimeric envelope genes were constructed that contain the antigen binding domain of an antibody at the amino terminus fused to the carboxy terminus of the envelope gene. Such particles may only bind to and infect target cells that contain an antigen structure which is recognized by the antibody moiety of the chimeric envelope protein.

FIG. 2 is a diagram illustrating plasmids expressing mutant envelope genes of spleen necrosis virus (SNV). Genes are expressed from the Rous sarcoma virus promoter (RSV/pro) and polyadenylated within the polyadenylation signal of herpes simplex virus thymidine kinase gene (TK/poly(A)). The polylinker of pBluescript was inserted between the promoter and the polyadenylation sequence to allow the easy cloning of genes into this vector (plasmid sequences that abut the vector are not shown). a/b) point mutations were introduced into the env gene by site directed mutagenesis to create new restriction enzyme recognition sites (indicated by an *). All enzymes cut exactly between two codons creating blunt ends for easy ligation without shifting the reading frame. c/d) chimeric envelope of containing an antigen binding peptide fused to the carboxy terminus of env. e) pJD214Hy, a retroviral vector used in all studies to test the transfer of genes by retroviral vector particles.

FIG. 3 shows the sequence of the single chain antibody gene (scFv) against the hapten DNP.

FIG. 4 illustrates retroviral packaging cells. A) A eucaryotic cell containing two different plasmids for the production of retroviral vector particle proteins. A retroviral vector transfected into such cells and carrying the gene of interest is encapsidated by retroviral core proteins. The envelope expression vectors expresses targeting envelopes (e.g., a antigen binding peptide fused to the envelope). Virus particles are produced that infect a target cell only that contains a receptor specific for the antigen binding site. The helper shown under B) is similar to that shown above except that it also contains a gene expression vector coding for the wild-type envelope. Virus particles produced from such helper cells contain "mixed" envelopes which consist of the targeting envelope and the wild-type envelope. Formation of mixed oligomers is possible because both, the targeting as well as the wild-type envelope contain a complete TM peptide which mediates the formation of oligomers.

FIG. 5 illustrates a eucaryotic gene expression vector (pTC13) to obtain high level of gene products that contain a ER recognition sequence. The vector shown has been derived from a another gene expression vector (termed pRD114) which is described in Sheay, W. et al., 1993. The vector shown differs from pRD114 in that it contains a gene fragment coding for a ER recognition signal sequence to enable the transport of proteins through the endoplasmatic reticulum. It contains two recognition sites for the restriction enzymes NruI and StuI which cut between two codons downstream of the ER signal sequence coding region. DNA fragments coding for any peptide can be inserted into this vector. Translation of the inserted gene is terminated by using one of the three stop codons. MLV-U3-pro: promoter and enhancer of murine leukemia virus; Ad.V.leader: tripartite leader sequence of adenovirus; SV40 poly(A): polyadenylation signal sequence of simian virus 40;

FIG. 6 illustrates plasmid vectors expressing targeting envelope proteins. The PCR product of the gene coding for the single chain antibody B6.2 (a Eco47III to NruI fragment, see Material and Methods) was cloned into the NruI site of pTC13 (FIG. 5) to give plasmid pTC23. Carboxy terminal parts of the SNV envelope gene were isolated and cloned into the NruI site downstream of the B6.2 antibody gene. The resulting targeting antibody-envelope fusion gene of pTC24 and pTC25 are similar to pTC4 and pTC5. pTC24 and pTC25 retain exactly the same amount of SNV envelope as pTC4 and pTC5, respectively. In pTC26 the antibody coding genes abuts the envelope coding region at codon 167 of the envelope gene. Plasmids pSNV-MLVchiC and pSNV-MLV-chiD are identical to pTC4 and pTC5, except that the antibody gene is replaced with a gene fragment encoding for almost the complete SU peptide of MLV. In these clones the ER transport signal sequence (L) is from MLV. MLV-pro: promoter and enhancer of murine leucemia virus; AVt1: tripartite leader sequence of adenovirus; L: ER transport signal sequence; B6.2scFV: gene encoding the single chain antibody B6.2; poly(A) polyadeylation signal sequence of SV40; SU surface peptide coding region of the SNV envelope; TM: transmembrane coding region of the SNV envelope; RSV: promoter and enhancer of Rous sarcoma virus.

APPENDIUM OF REFERENCES

Albritton, L. M., Tseng, L. Scadden, D., and Cunningham, J. M. 1989. A putative murine ecotropic retrovirus receptor gene encodes a multiple membrane-spanning protein and confers susceptibility to virus infection. Cell 57:659–666.

Battini, J. L. Heard, J. M., and Danos, O. (1992) Receptor choice in the envelope glycoproteins of amphotropic, xenotropic, and polytropic murine leukemia viruses. J. Virol. 66: 1468–1475.

Bird, R. E., Hardman, K. D., Jacobson, J. W., Johnson, S., Kaufman, B. M., Lee, S. -M., Lee, T., Pope, S. H.. Riordan, G. S., and Whitlow, M 1988. Single-chain antigen binding proteins. Science, 242; 423–426

Colcher, D., Bird, R., Roselli, M., Hardman, K. D., Johnson, S, Pope, S., Dodd, S. W., Pantoliano, M. W., Milenic, D. E. Schlom, J. 1990. in vitro tumor targeting of a recombinant single chain antigen-binding protein. J. Natl. Canc. Inst. 82:1191–1197.

Cone, R. D. and Mulligan, R. C. 1984. High-effiency gene transfer into mammallian cells: generation of helper-free recombinant retrovirus with broad mammallan host range. Proc. Natl. Acad. Sci. USA 81:6349–6353.

Cournoyer, D., Scarpa, M., Jones, S. N., Moore, K. A., Belmont, J. W., and Caskey, C. T, 1990. Gene therapy: a new approach for the treatment of genetic disorders. Clin. Pharmacol. Ther. 47(1): 1–11.

Danos, O. and Mulllgan, R. G. 1988. Safe and efficient generation of recombinant retroviruses with amphotropic and ecotropic host ranges Proc, Natl. Acad. Sci. 85: 6460–6464.

Davies, M. M. and Metzger, H. 1983. Structural basis of antibody function. Annu. Rev. Immunol. 1:87 117.

Dougherty, J. P. and Temin, H. M. 1989. New retrovirus helper cells with almost no nucleotide sequence homology to retrovirus vectors. J. Virol. 63, 3209–3212.

Friedmann, T. 1989. Progress toward human gene therapy. Science 244, 1275–1281.

Gritz, L., and J Davies 1983. Plasmid encoded hygromycin B resistance: the sequence of hygromycin B phosphotransferase gene and its expression in *Escherichia coli* and *Saccharomyces cerevisiae*. Gene 25, 179–188.

Hunter, E. and Swanstrom. R 1990. Retrovirus envelope glycoproteins. Curr. Top. Microbiol. Immunol. 157:187–253.

Kohn, D. B., Anderson, W. F., and Blaese, M. B. 1989. Gene therapy for genetic diseases. Cancer Inbestigation 7(2):179–192.

Larson, S. M. 1990. Improved tumor targeting with radiolabeled, recombinant, single-chain, antigen-binding protein. J. Natl. Canc. Inst. 82: 1189–1190.

Markowitz, D., Goff, S., and Bank, A. 1988 A safe packaging line for gene transfer: separation of viral genes on two different plasmids. J. Virol. 62:1120–1124.

Mikawa, T., D. A. Fischman, J. P. Dougherty, and A. M. C. Brown. In vivo analysis of a new lacZ retrovirus vector suitable for lineage marking in avian and other species. Exp. Cell Res. 195: 516–523.

Miller, A. D. 1990. Progress toward human gene therapy. Blood 76(2) 271–278.

Mims, C. A. 1986. Virus receptors and cell tropism. J. Infect. 12:199–204.

Ott, D., and Rein, A. 1992. Basis for receptor specificity of nonecoptropic murine leukemia virus surface glycoprotein gp70SU. J. Virol. 66:4632–4638.

Riley, S. C., Connors, S. J., Klinman, N. R., and Ogata, R. T. 1986. Preferential expression of variable region heavy chain gene segments by predominant 2,4-dinitrophenyl-specific BALB/c nneonatal antibody clonotypes. Proc. Natl. Acad. Sci. 83:2589–2593. Rolt,1. 1988. In "Essential Immunology". Blackwell Scientific Publications.

Sheay, W., S. Nelson, I. Martinez. T. H. T. Chu., S. Bathia, and R. Dornburg. 1993. Downstream insertion of the adenovirus tripartite leader sequence enhances expression in universal eucaryotic vectors. Biotechniques. 15: 856–861.

Shinnick, T. M., Lerner, R. A., and Sutcliffe, J. G. 1981. Nucleotide sequence of Moloney murine leukemia virus. Nature 293:543–548.

Temin, H. M. 1986. Retrovirus vectors for gene transfer: efficient integration into and expression of exogenous DNA in vertebrate cell genomes, in "Gene Transfer" (R. Kucherlapatl, ed.) Plenum Press, New York.

Varmus, H. E., and Brown, P. 1988 Retroviruses, in "Mobile DNA" (M. Owe and D. Berg, eds.) ASM, Washington DC.

Watanabe, S., and H. M. Temin. 1983, Construction of a helper cell line for avian reticulonendotheliosis virus cloning vectors. Mol. Cell. Biol. 3, 2241–2249.

Weiss, R,, Teich, N., Varmus, H., and Coffin, J. 1985. RNA tumor viruses. Cold spring harbor Laboratory, Cold Spring Harbor, N.Y.

Whitlow, M, and Filpula, D., Single-chain Fv proteins and their fusion proteins. Methods: A comparison to methods In Enzymology. Vol. 2 pp 1–9.

Throughout this application, various publications have been referenced. The disclosures in these publications are incorporated herein by reference in order to more fully describe the state of the art.

The invention being thus described. it will be obvious that the same may be varied in many ways. Such variations are not to be regarded as a departure from the spirit and scope of the invention and all such modifications are intended to be included within the scope of the following claims.

I claim:

1. A retroviral vector particle having target cell specificity which comprises a retroviral vector having a targeting peptide fused to the envelope protein of the retroviral vector to form a targeting envelope, wherein the targeting peptide replaces or disrupts the natural viral receptor binding site and the targeting peptide is the antigen binding site of an antibody, the receptor binding peptide of another virus, or is a peptide that specifically binds to a specific receptor of the target, and wherein the retroviral vector particle is spleen necrosis virus.

2. The retroviral vector particle according to claim 1, wherein the targeting peptide is a single chain antibody against the hapten dinitrophenol (anti-DNP-scFv).

3. The retroviral vector particle according to claim 1, wherein the targeting peptide is an antigen binding site directed against a cell-surface protein of the target cell.

4. The retroviral vector particle according to claim 1, wherein the targeting peptide is the receptor binding peptide of another virus.

5. The retroviral vector particle according to claim 1, wherein the retroviral vector comprises a targeting envelope and a wild-type envelope.

* * * * *